US00RE38892E

(19) United States
(12) Reissued Patent
Ryu

(10) Patent Number: US RE38,892 E
(45) Date of Reissued Patent: Nov. 29, 2005

(54) HAMMER HANDLE

(75) Inventor: Suk-Ho Ryu, Seoul (KR)

(73) Assignee: Wavex Corporation, Toronto (CA)

(21) Appl. No.: 29/158,950

(22) Filed: Apr. 10, 2002

Related U.S. Patent Documents

Reissue of:
(64) Patent No.: Des. 422,472
Issued: Apr. 11, 2000
Appl. No.: 29/096,561
Filed: Nov. 13, 1998

(51) LOC (8) Cl. ..... 08-02
(52) U.S. Cl. ..... D8/80
(58) Field of Search ..... D8/75, 76, 77, D8/78, 79, 80, 81, 107; 81/19, 20, 21, 22, 23, 24, 25; 7/143; 16/110 R

(56) References Cited

U.S. PATENT DOCUMENTS

| | | | | | |
|---|---|---|---|---|---|
| 479,032 | A | * | 7/1892 | Surbaugh | 81/22 |
| 1,341,378 | A | * | 5/1920 | McKenzie | 81/22 |
| 1,401,896 | A | * | 12/1921 | Ehrhart | 81/22 |
| 2,155,804 | A | * | 4/1939 | Rubin | 81/20 |
| D139,475 | S | * | 11/1944 | Laughlin | D8/80 |
| D157,883 | S | * | 3/1950 | Maxwell | D8/80 |
| D182,076 | S | * | 2/1958 | MacMinn | D8/77 |
| D182,077 | S | * | 2/1958 | MacMinn | D8/77 |
| D185,675 | S | * | 7/1959 | MacMinn | D8/80 |
| D288,897 | S | * | 3/1987 | Kalberer | D8/80 |
| D300,111 | S | * | 3/1989 | Square | D8/75 |
| D302,515 | S | * | 8/1989 | Kandel | D8/81 |
| D315,483 | S | * | 3/1991 | Williamson | D8/75 |
| D402,175 | S | * | 12/1998 | Sellers | D8/75 |

* cited by examiner

*Primary Examiner*—Philip S. Hyder
(74) *Attorney, Agent, or Firm*—Maria Parrish Tungol

(57) CLAIM

The ornamental design for a hammer handle, as shown and described.

DESCRIPTION

FIG. 1 is a perspective view of a hammer handle showing my new design;
FIG. 2 is a bottom plan view thereof;
FIG. 3 is a top plan view thereof;
FIG. 4 is a right side elevational view thereof;
FIG. 5 is a rear elevational view thereof; and,
FIG. 6 is a front elevational view thereof.
The left side of the hammer handle is a mirror image of the right side.
The hammer head and grip shown in broken lines FIGS. 1–6 are not part of the claimed design.

1 Claim, 2 Drawing Sheets

Matter enclosed in heavy brackets [ ] appears in the original patent, but forms no part of this reissue; matter printed in italics indicates the additions made by reissue.

(Amended)

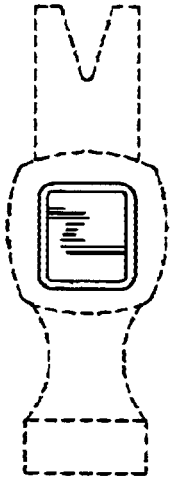
FIG.2 (Amended)
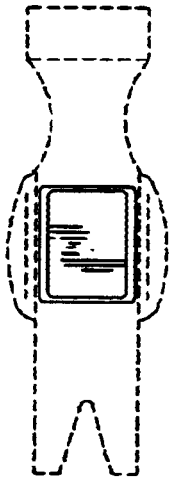
FIG.3 (Amended)
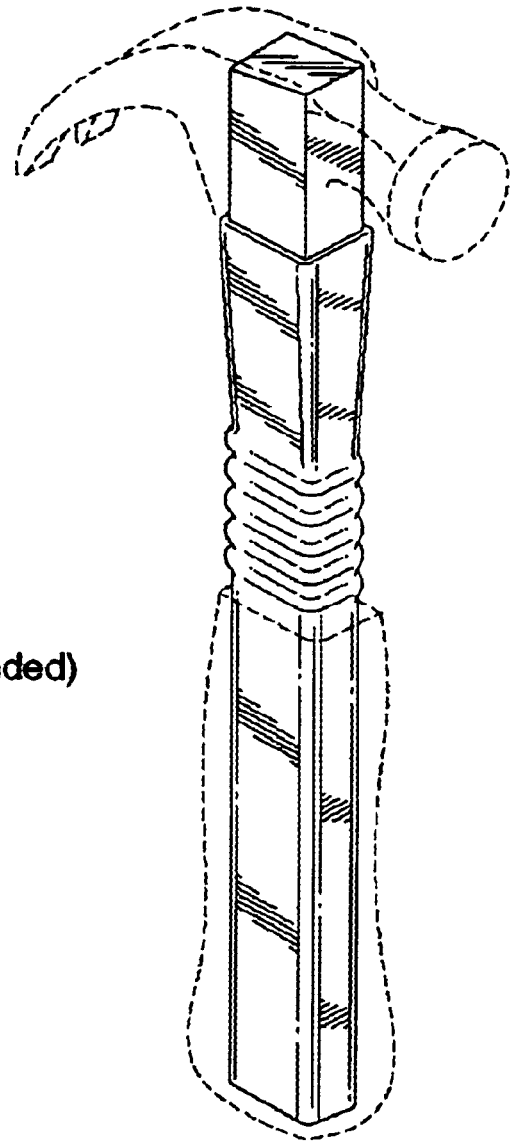
FIG.1 (Amended)

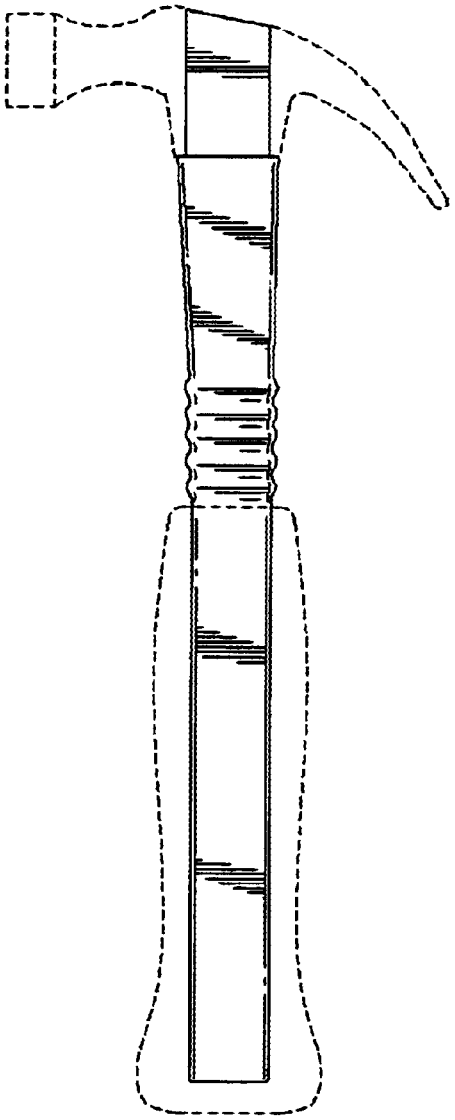
FIG.4
(Amended)
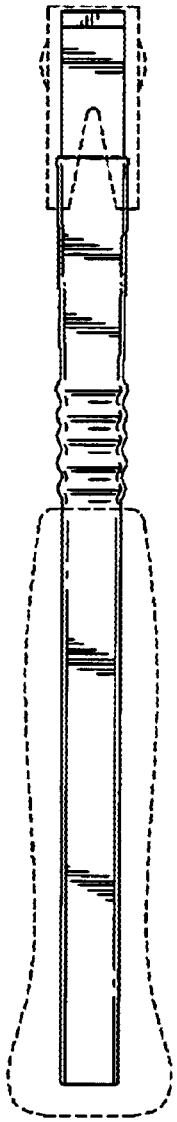
FIG.5
(Amended)
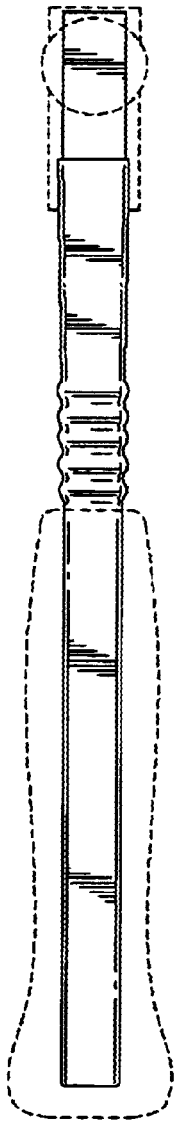
FIG.6
(Amended)